(12) United States Patent
Gibson et al.

(10) Patent No.: US 6,215,000 B1
(45) Date of Patent: Apr. 10, 2001

(54) CRYSTALLINE COMPLEXES OF BACCATIN III WITH IMIDAZOLE, 2-METHYLIMIDAZOLE OR ISOPROPANOL

(75) Inventors: Francis S. Gibson, Dayton, NJ (US); Jianmei Wei, San Diego, CA (US); John L. Dillon, Jr.; Purushotham Vemishetti, both of East Syracuse, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/537,193

(22) Filed: Mar. 28, 2000

Related U.S. Application Data

(63) Continuation of application No. 09/226,451, filed on Jan. 6, 1999.
(60) Provisional application No. 60/071,325, filed on Jan. 14, 1998.

(51) Int. Cl.⁷ .................. C07D 233/54; C07D 305/14; C07D 407/00; C07D 493/00; C12P 17/02
(52) U.S. Cl. .................. 548/311.1; 435/123; 549/510
(58) Field of Search .................. 548/311.1; 549/510; 435/123

(56) References Cited

U.S. PATENT DOCUMENTS

| | | | |
|---|---|---|---|
| 4,924,012 | * 5/1990 | Colin et al. | 549/510 |
| 5,202,448 | * 4/1993 | Carver et al. | 549/510 |
| 5,264,591 | * 11/1993 | Bombardelli et al. | 549/214 |
| 5,274,124 | 12/1993 | Holton | 549/214 |
| 5,399,726 | * 3/1995 | Holton et al. | 549/510 |
| 5,407,816 | 4/1995 | Bringi et al. | 435/123 |
| 5,475,120 | * 12/1995 | Rao | 549/510 |
| 5,478,736 | 12/1995 | Nair | 435/123 |
| 5,578,739 | * 11/1996 | Hittinger | 549/510 |
| 5,580,997 | * 12/1996 | Bouchard et al. | 549/510 |
| 5,618,538 | 4/1997 | ElSohly et al. | 424/195.1 |
| 5,637,484 | 6/1997 | Yukimune et al. | 435/123 |
| 5,736,366 | 4/1998 | Margraff | 435/123 |
| 5,808,102 | 9/1998 | Poss et al. | |

OTHER PUBLICATIONS

Commercon, A., et al, Tetrahedron Lett., vol. 33, No. 36, pp. 5185–5188, 1992.
Dennis, J.N., et al, J. Am. Chem. Soc., 110, 5917–5919, 1988.
Kingston, D.G.I., et al, Tetrahedron Lett., vol. 35, No. 26, pp. 4483–4484 1994.
Wani, M.C., et al, J. Am. Chem. Soc., 93:9, pp. 2325–2327, 1971.
Witherup et al, J. Liq. Chromatogr., 12 (11), 2117–32 (1989).

* cited by examiner

*Primary Examiner*—Floyd D. Higel
(74) *Attorney, Agent, or Firm*—Gabriel Lopez

(57) ABSTRACT

Disclosed are crystalline complexes of baccatin III with imidazole, 2-methylimidazole or isopropanol, which are useful for isolating baccatin III from plant tissue cell culture and plant extracts containing baccatin III.

20 Claims, No Drawings

CRYSTALLINE COMPLEXES OF BACCATIN III WITH IMIDAZOLE, 2-METHYLIMIDAZOLE OR ISOPROPANOL

This is a continuation of application Ser. No. 09/226,451, Jan. 6, 1999, pending. This application claims priority from provisional U.S. Application Ser. No. 60/071,325, filed Jan. 14, 1998, incorporated herein by reference in its entirety.

BACKGROUND OF THE INVENTION

The present invention is directed to novel crystalline complexes of baccatin III with imidazole, 2-methylimidazole or isopropanol which are useful for isolating and purifying baccatin III from a crude plant cell culture solution. The complex is also useful for isolation and purification of baccatin III from crude extracts of bark and leaves of the plant, such as *Taxus bevifolia* (Western yew) *Taxus baccata* etc, which contain baccatin III with other impurities or from plant tissue culture (PTC) solutions.

The taxane family of terpenes, of which baccatin III is a member, is of considerable importance, since the latter is a starting material for the semi-synthesis of paclitaxel (Taxol®). Paclitaxel (Taxol®) is now considered one of the most promising treatments for breast and ovarian cancer. Its effectiveness is also demonstrated against lung cancer and melanoma.

The isolation of baccatin III from the Yew needles has been described in U.S. Pat. Nos. 9,330,696, 930,312. According to the method of these U.S. Pat. Nos. 9,330,696, 930,312, Yew needles are dewaxed with a critical or nearly critical fluid, followed by extraction of the taxoids with a mixture of critical or nearly critical fluid and a polar solvent and the resulting extract is chromatographed. The chromatography is carried out using two columns. The first column, a normal-phase silica absorption column, retains the taxoids and the second column, a reverse-phase absorption column, separates the taxoids. The taxoids, such as taxol, baccatin III, 10-deacetylbaccatin III and cephalomannine, are eluted with a mixture of critical or nearly-critical fluid and a polar solvent. Patents describing the production of baccatin III and paclitaxel PTC solutions are U.S. Pat. No. 5,407,816 and U.S. 5,637,484.

Another method for the isolation of baccatin III has been described in J. Liq, chromatogr., 12 (11), 2117–32 (1989). In this method, large quantities of methanol extracts derived from the bark of the Western yew, *Taxus brevifolia* and containing a mixture of five taxanes was resolved on adsorbent types (cyano and Ph bonded silica gel phases) using isocratic and gradient elution. The five taxanes obtained were, namely, Taxol, cephalomannine, 10-deacetylcephalomannine, baccatin III and 10-deacetylbaccatin III.

In addition, an improved method for isolating Taxol and certain clinically important analogs of Taxol including baccatin III has been described in U.S. Pat. No. 5,475,120. The improved method which comprises treating the crude extract of a naturally occurring Taxus species by reverse phase liquid chromatography on an adsorbent, causing the taxol and taxol analogs to be adsorbed on the adsorbent and recovering the taxol and its analogs from the adsorbent by elution with an eluant. The compounds isolated were taxol, 10-deacetylbaccatin III, baccatin III etc.

Thus, all of the above processes require an alcoholic extract or a polar solvent extract obtained from the bark or needles of the Taxus species and then chromatographing the crude extract on a column of silica gel.

SUMMARY OF THE INVENTION

An object of the present invention is to provide a novel crystalline complex of baccatin III and imidazole, 2-methylimidazole or isopropanol, when baccatin III is mixed together in solution with either imidazole, 2-methylimidazole or isopropanol. Another object of the present invention is to provide a method of isolating baccatin III from plant cell culture extracts containing a mixture of several taxanes including baccatin III by treating the cell culture with imidazole, 2-methylimidazole or isopropanol and collecting the precipitated complex of baccatin III and imidazole, 2-methylimidazole or isopropanol. This precipitated complex of baccatin III and imidazole, 2-methylimidazole or isopropanol is then broken down to give baccatin III.

Another additional object of the present invention is to provide a method of isolating baccatin III from plant extracts of bark of *Taxus brevifolia* or needle (leaves) or any plant extract containing baccatin III in admixture with several other taxanes. The extract of bark or needles is treated with imidazole, 2-methylimidazole or isopropanol and the precipitated complex of baccatin III and imidazole, 2-methylimidazole or isopropanol is collected and broken down to give baccatin III.

Another object of the present invention is to purify crude baccatin III solid containing other taxanes by heating it in isopropanol to form a solution and then allowing it to cool to form a complex of baccatin III with isopropanol.

DETAILED DESCRIPTION OF THE INVENTION

Briefly, therefore, the present invention is directed to a novel crystalline complex of baccatin III and imidazole (I), 2-methylimidazole (II) or isopropanol (III) having the structural formulas:

I 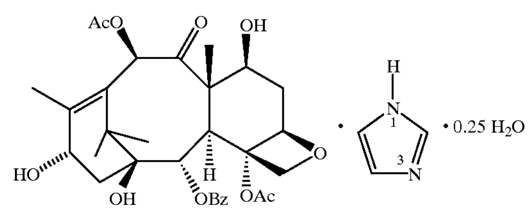 or

II 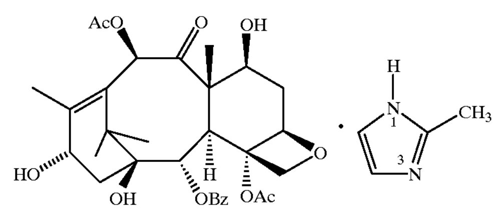 or

III

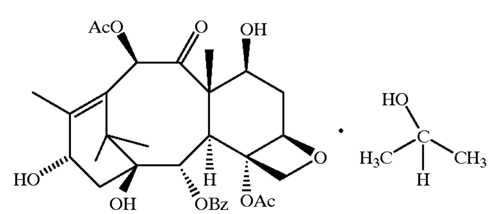

The x-ray structure of the three complexes (IA, IIB, IIIC) are determined by a single crystal x-ray analysis and are depicted herein below.

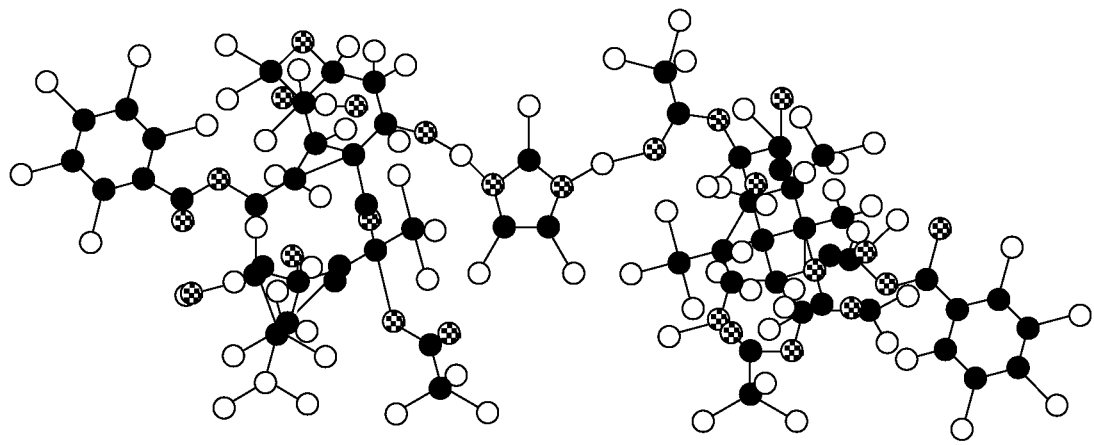
IA
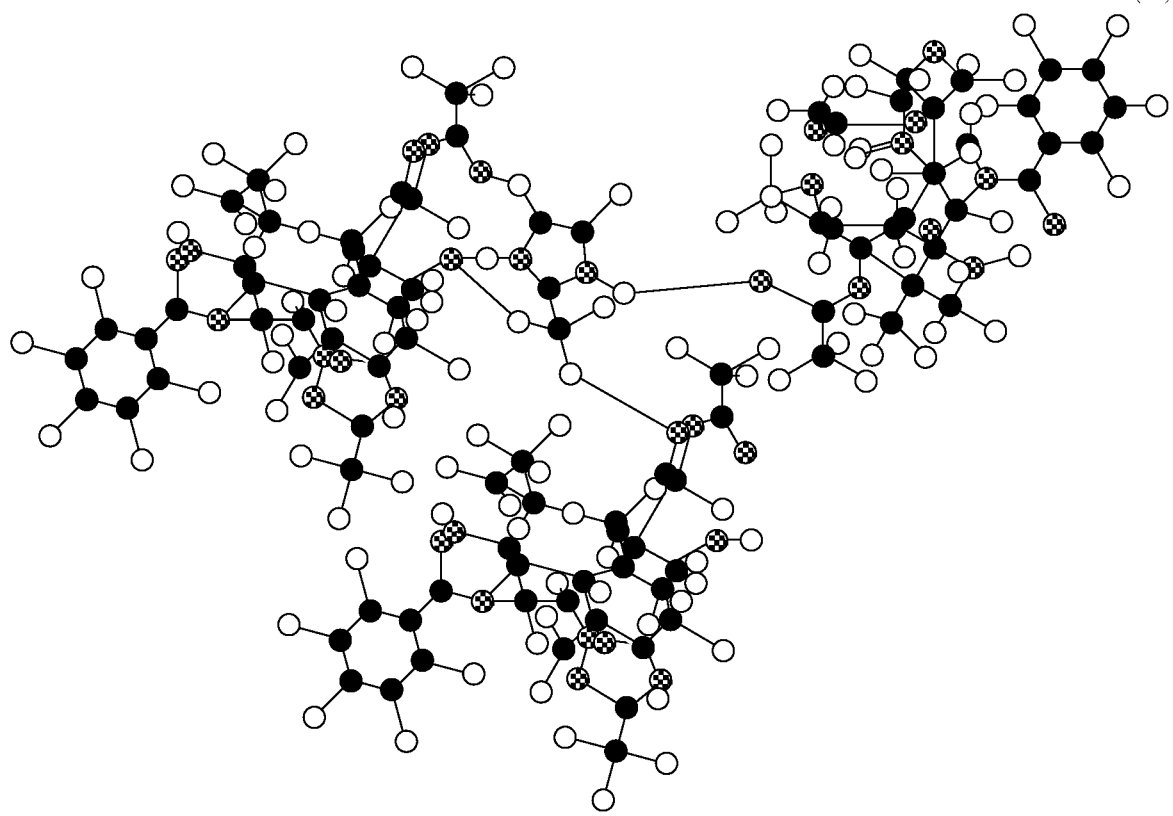
(IIB)

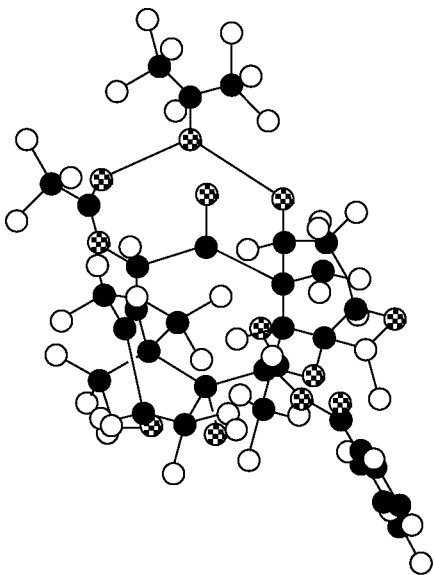

IIIC

The x-ray analysis shows the above chemical structure of baccatin III and imidazole with a molecular formula of $C_{37}H_{38}O_{11}\cdot C_3H_4N_2\cdot 0.25H_2O$. In the crystal, two hydrogen bonds are formed between baccatin III and imidazole, O7-H—N=1.743 Å) and N1-H—O (the carbonyl oxygen of the C-10 acetyl group) (154.0°, N—O=2.898 Å, H—O=2.000 Å). The water molecule also forms two hydrogen bonds with baccatin III, Owater-H—O1 (O—O=2.750 Å) and Owater-H—O13 (O—O=3.060 Å).

The x-ray analysis shows the chemical structure of baccatin III and 2-methylimidazole with a molecular formula of $C_{31}H_{38}O_{11}\cdot C_4H_6N_2$. Similar to imidazole, the 2-methylimidazole complex links molecules of baccatin III through two hydrogen bonds, O7-H—N3 (171.4°, O—N=2.671 Å, H—N=1.680 Å) and W1-H—O (the carbonyl oxygen of the C-10 acetyl group) (148.5°, N—O=2.960 Å, H—O=2.155 Å). The 2-methylimidazole also interacts with baccatin III via three C—H—O hydrogen bonds, two of them involving the methyl group.

The x-ray analysis shows the chemical structure of baccatin III and isopropanol complex with a molecular formula of $C_{31}H_{38}O_{11}\cdot C_3H_3O$. There are two hydrogen bonds formed between baccatin III and isopropanol.

The single crystal of the complexes of imidazole and 2-methylimidazole are grown in the solvent acetonitrile. The single crystal of the complex of isopropanol is grown in methylene chloride and isopropanol.

The x-ray powder diffraction pattern of the three complexes, namely baccatin III-imidazole, baccatin III-2-methylimidazole or baccatin III-isopropanol were obtained using a Debye-Scherrer powder camera irradiated by copper targer x-ray tube for 2 hours at 40 kv, 20 ma through a nickel filter.

The d-spacings and the relative intensities of the three complexes are tabulated below.

TABLE 1

Baccatin III-imidazole complex

| Line | Spacings D(Å) | Relative Intensity I/Io |
|---|---|---|
| 1 | 10.52 | 30 |
| 2 | 9.57 | 30 |
| 3 | 8.95 | 100 |
| 4 | 6.95 | 20 |
| 5 | 6.60 | 10 |
| 6 | 6.24 | 20 |
| 7 | 5.61 | 10 |
| 8 | 5.20 | 40 |
| 9 | 4.82 | 40 |
| 10 | 4.13 | 50 |
| 11 | 3.90 | 20 |
| 12 | 3.75 | 10 |

TABLE 2

Baccatin III-2-methylimidazole complex

| Line | Spacings D(Å) | Relative Intensity I/Io |
|---|---|---|
| 1 | 10.52 | 30 |
| 2 | 9.41 | 30 |
| 3 | 8.70 | 100 |
| 4 | 6.72 | 20 |
| 5 | 6.13 | 20 |
| 6 | 5.50 | 10 |
| 7 | 5.09 | 30 |
| 8 | 4.69 | 30 |
| 9 | 4.28 | 10 |
| 10 | 4.14 | 40 |
| 11 | 3.89 | 10 |
| 12 | 3.75 | 20 |
| 13 | 3.73 | 10 |

TABLE 3

Baccatin III-isopropanol complex

| Line | Spacings D(Å) | Relative Intensity I/Io |
|---|---|---|
| 1 | 10.52 | 30 |
| 2 | 9.24 | 20 |
| 3 | 8.52 | 100 |
| 4 | 7.19 | 20 |
| 5 | 6.60 | 20 |
| 6 | 6.13 | 20 |
| 7 | 5.35 | 10 |
| 8 | 5.03 | 30 |
| 9 | 4.70 | 25 |
| 10 | 4.09 | 50 |
| 11 | 3.78 | 20 |
| 12 | 3.72 | 20 |
| 13 | 3.56 | 20 |
| 14 | 3.24 | 10 |
| 15 | 3.12 | 10 |
| 16 | 2.95 | 10 |
| 17 | 2.83 | 20 |

The complex is formed by dissolving baccatin III having the structural formula in dichloromethane or another appropriate organic solvent such as n-butyl acetate, ethyl acetate, or dichloroethane, at room temperature and then adding to the solution, with stirring, imidazole or 2-methylimidazole as a solid or in a solution of organic solvent, such as dichloromethane. In the case of isopropanol, the baccatin III is dissolved directly in the solvent by heating and then allowed to cool to crystallize the complex. The solution is stirred at room temperature and the precipitated crystalline complex is collected on a filter paper. The yield of the complex is 89% with imidazole, 83% with 2-methylimidazole and 77% with isopropanol. The crystalline complex contains baccatin Ill and imidazole, 2-methylimidazole or isopropanol in a molar ratio of 1:1. The complex of baccatin III and imidazole or 2-methylimidazole can be broken down to liberate baccatin III. The complex is stirred in a mixture of an organic solvent, for example methylene chloride and water for about 30 minutes. Then the organic layer of methylene chloride is separated, washed with water a couple of times, dried and then evaporated to dryness. The recovery of pure baccatin III obtained is 99%. In the case of baccatin III-isopropanol complex, it can be broken by heating the solid in a solvent such as acetonitrile.

The compounds baccatin III and imidazole, 2-methylimidazole or isopropanol are available commercially.

The usefulness of the complex is to liberate baccatin III from plant cell culture or plant extracts containing baccatin III in admixture with other taxanes without the need of resorting to tedious column chromatography. Among the several amines tested such as methyl-4-imidazole carboxylate, 1-methylimidazole, histamine and imidazole or 2-methylimidazole in their ability to form a complex with baccatin III, only imidazole and 2-methylimidazole selectively form a complex with baccatin III. The other amines did not form a complex with baccatin III.

The present invention is also directed to a process for isolating baccatin III from organic plant cell culture broth extracts containing baccatin III in admixture with other taxanes, including paclitaxel (Taxol®). The process comprises treating a plant cell culture broth extract in an organic solvent, such as n-butyl acetate with imidazole, 2-methylimidazole or isopropanol and collecting the precipitated crystalline complex by filtration. The complex is then treated with a mixture of methylene chloride and $H_2O$, the organic methylene chloride layer separated, worked with water, dried and evaporated to dryness to obtain solid crystalline baccatin III.

The plant cell culture broth was obtained from Phyton Inc., Ithaca, N.Y.

The present invention is also directed to a process for isolating baccatin III from organic plant extracts of bark or needles of yew trees which contain baccatin III in admixture with other taxanes, including paclitaxel (Taxol®). The process comprises treating the organic plant extract with imidazole or 2-methylimidazole and collecting the precipitated crystalline complex by filtration. The baccatin III is liberated from the complex by treating with a mixture of an organic solvent, such as methylene chloride and water, separating the organic methylene chloride layer, drying and then evaporating to dryness to obtain baccatin III in crystalline form.

The following examples illustrate the invention.

EXAMPLE 1

Preparation of the Complex of Baccatin III with Imidazole

To a stirred solution of 250 mg (0.426 mmole) of baccatin III (purchased from Hauser Co.) in 6 ml of $CH_2Cl_2$ at room temperature was added a solution of 32 mg (0.469 mmole) of imidazole (purchased from Aldrich Chemical Co.) in 1 ml of $CH_2Cl_2$. The resulting solution was stirred at room temperature for 30 minutes and then the precipitated crystalline complex of baccatin III and imidazole was collected by filtration and dried to give 247 mg of the complex. The yield of the complex was 89%. NMR (acetone) 68.2–8.1 (m, 2 H), 7.7–7.5 (m, 4H), 7.1 (s, 2H), 6.5 (s, 1H), 5.7 (d, 1H, J=7.2), 5.6 (s, 0.5H), 5.0–4.9 (m, 2.5H), 4.5–4.4 (m, 1H), 4.2 (s, 2H), 3.96 (d, 1H, J=6.8), 3.7 (s, 1H), 3.0–2.3 (m, 4H), 2.3 (s, 3H), 2.2 (s, 3H), 2.1 (s, 3H), 2.1–2.0 (m, 1H), 2.9–2.7 (m, 1H), 1.7 (s, 3H), 1.2 (s, 3H), 1.1 (s, 3H).

EXAMPLE 2

Liberation of Baccatin III from the Complex of Example 1

To a complex of 200 mg (0.305 mmole) of Example 1 was added at room temperature with stirring 6 ml of $CD_2Cl_2$ and 2 ml of $D_2O$. The resulting solution was stirred for 30 minutes at room temperature. At 5, 15 and 30 minute intervals, samples were withdrawn from the solution for NMR analysis. The NMR analysis of the sample taken at 5 minutes showed that the complex was completely broken. After 30 minutes, the organic $CD_2Cl_2$ layer was separated, the water layer was washed once with 5 ml portion of $CD_2Cl_2$ and separated. The separated 5 ml portion of $CD_2Cl_2$ was combined with the original layer of $CD_2Cl_2$, dried and then concentrated to give 178 mg (99%) of baccatin III.

EXAMPLE 3

Preparation of the Complex of Baccatin III with Imidazole from a Cell Culture Extract Containing Baccatin III in Admixture with Other Taxanes A whole broth mixture approximately (400 L) derived from plant tissue culture, obtained for example by U.S. Pat.

No. 5,407,816, containing 200 mcg/ml of baccatin III was extracted with a solution containing 7% acetic acid and 93% of a mixture of 15% isopropanol in butyl acetate. The resulting organic solution was washed with water and concentrated under vacuum to approx. 70 L and diluted with 10% heptane. The solution was passed through a column containing 40L of alumina packed using 20% butanol in butyl acetate and equilibrated with butyl acetate. The column was eluted successively with 100 L of butyl acetate and 150 L of 2.5% butanol in butyl acetate. A portion of the desired fractions containing baccatin III were combined and concentrated to afford a butyl acetate solution of baccatin III assaying at approximately 18 mg/ml.

A 4.5 ml aliquot of the n-butyl acetate solution was concentrated to 2 ml. With stirring at room temperature, 11 mg (0.16 mmole) of imidazole were added. After stirring for five minutes, a precipitate was observed. An additional 11 mg (0.16 mmole) of imidazole was added to the mixture and the mixture was stirred for twenty-five minutes. The mixture was cooled to 0° C. and stirred for one hour. The precipitated solid was collected on a filter and dried to yield 60 mg (67%) of solid which was a complex of baccatin III and imidazole as evidenced by NMR data (refer to ex. 1).

EXAMPLE 4

Attempted Preparation of the Complex of Baccatin III with 1-methylimidazole

To a stirred solution of 100 mg (0.17 mmole) of baccatin III in 6 ml of $CH_2Cl_2$ at room temperature, was added 30 µl (0.187 mmole) of 1-methylimidazole. The solution was stirred for 30 minutes and then evaporated to dryness. The obtained solid was not a complex of baccatin III and 1-methylimidazole as evidenced by NMR.

EXAMPLE 5

Attempted Preparation of Baccatin III Complex with Methyl-4-imidazole Carboxylate To a stirred solution of 100 mg (0.17 mmole) of baccatin III in 6 ml of CH2Cl2 at room temperature, was added 23.6 mg (0.187 mmole) of methyl 4-imidazole carboxylate in 800 µl of methanol. The solution was stirred for 3 hours at room temperature and then evaporated to dryness. The solid obtained was not a complex of baccatin III and methyl 4-imidazole carboxylate as shown by NMR.

EXAMPLE 6

Attempted Preparation of Baccatin III Complex with Histamine

To a stirred solution of 100 mg (0.17 mmole) of baccatin III at room temperature, was added a solution of 20.8 mg of histamine (0.187 mmole) in 800 µl of methanol. The solution was stirred for 3 hours at room temperature and then evaporated to dryness. The obtained solid was not a complex of baccatin III and histamine as shown by NMR data.

EXAMPLE 7

Baccatin III-2-methylimidazole Complex

Baccatin III (144 mg, 0.246 mmol) was dissolved in 4 mL of dichloromethane with stirring. 2-methylimidazole (26 mg, 130 mol %) was added and it dissolved quickly. After about 1 minute a precipitate began to form. The reaction was cooled to 0° C. for 15 min and filtered to collect 141 mg (83%) of baccatin III-2-methylimidazole complex.

NMR data for the baccatin III 2-methylimidazole complex: (chloroform) δ 7.9–7.2 (m, 5H), 6.75 (s, 2H), 6.13 (s, 1H), 5.43 (d, 1H, J=7.2), 4.79 (d, 1H, J=8.1), 4.69 (t, 1H, J=7.3), 4.29 (dd, 1H, J=6.8, 10.8),4.11 (d, 1H, J=8.1), 3.96 (d, 1H, J=8.1), 3.69 (d, 1H, J=6.7), 3.9 (br s, 1H), 2.40–2.30 (m, 1H), 2.25 (s, 2H), 2.13–2.08 (m, 5H), 2.05 (s, 3H), 1.97 (s, 3H), 1.97 (s, 4H), 1.86 (s, 3H), 1.71–1.62 (m, 1H), 1.48 (s, 3H), 0.92 (s, 6H).

EXAMPLE 8

Baccatin III-isopropanol Complex

Baccatin III (100 mg, 0.17 mmol) was dissolved in dichloromethane (4 mL). Isopropanol was added (130 uL, 1000%), and the resulting solution was allowed to stir for 1 h. Hexane was added to the cloud point, and crystallization began. The baccatin III, 2-propanol complex (85 mg, 77%) was collected by filtration.

EXAMPLE 9

Preparation of Complex of Baccatin III with Isopropanol from a Cell Culture Extract Containing Baccatin III in Admixture with Other Taxanes A 10.0 ml aliquot of a cell culture extract in n-butyl acetate containing 18 mg/ml (see Ex. 3) baccatin III was concentrated to dryness. The residue was dissolved in 3 ml of isopropanol at 50° C. After stirring the solution at room temperature for one hour, a precipitate was observed. The mixture was stirred at room temperature overnight. The precipitated solid was collected on a filter and dried to yield 156 mg (87%). The solid was a complex of baccatin III and isopropanol as evidenced by NMR data.

NMR data for the baccatin Ill-isopropanol complex: (chloroform) 6 7.91–7.30 (m, 5H), 6.13 (s, 1H), 5.45 (d, 1H, J=6.7), 4.80 (d, 1H, J=8.1), 4.70 (t, 1H, J=7.7), 4.29 (dd, 1H, J=6.7, 10.8), 4.12 (d, 1H, J=8.6), 3.98 (d, 1H, J=8.6), 3.85 (m, 0.6H), 3.70 (d, 1H, J=6.8), 3.55 (m, 0.4H), 2.45–0.90 (m, 32H).

EXAMPLE 10

Preparation of a Single Crystal of the Complex of Baccatin III and Imidazole and its X-ray Analysis A single crystal of the complex of baccatin III and imidazole was prepared by growing a crystal obtained in Example 1, in acetonitrile. The crystallization procedure, the data collection and the crystal data are given below.

Crystallization:

Crystal source: $CH_3CN$

Crystal description: Colorless thick plate

Crystal size (mm): 0.10×0.35×0.42

Date Collection:

Temperature (K): 295

°max(°): 75 (CUKα)

No. of reflections measured: 3894

No. of independent reflections: 3894

No. of observed reflections (I 3σ): 3266

Absorption correction ($^T$min-$^T$max): 0.88–1.00

$^R$int 0.00

Crystal Data:

Chemical formula: $C_{31}H_{38}O_{11}$—$C_3H_4N_2$.$0.25H_2O$

Crystal system: Orthorhambic

Space Group: $P2_12_12$

| | |
|---|---|
| a = 9.2771(4) Å | α = 90° |
| b = 41.215(2) Å | β = 90° |
| c = 8.5788(4) Å | γ = 90° |
| Z = 4 | $d_x$ = 1.325 g cm$^{-3}$ |
| V = 3280.1(2) Å$^3$ | |

No. Of reflections for lattice parameters: 25

ø range for lattice parameters (°): 15.93–42.58

Absorption coefficient (mm$^{-1}$): 0.79

The single crystal was subjected to x-ray analysis using an x-ray diffractometer. The resulting x-ray structure is given below:

| Line | Spacing d (Å) | Relative Intensity |
|---|---|---|
| 1 | 10.52 | 30 |
| 2 | 9.41 | 30 |
| 3 | 8.70 | 100 |
| 4 | 6.72 | 20 |
| 5 | 6.13 | 20 |
| 6 | 5.50 | 10 |
| 7 | 5.09 | 30 |
| 8 | 4.69 | 30 |
| 9 | 4.28 | 10 |
| 10 | 4.14 | 40 |

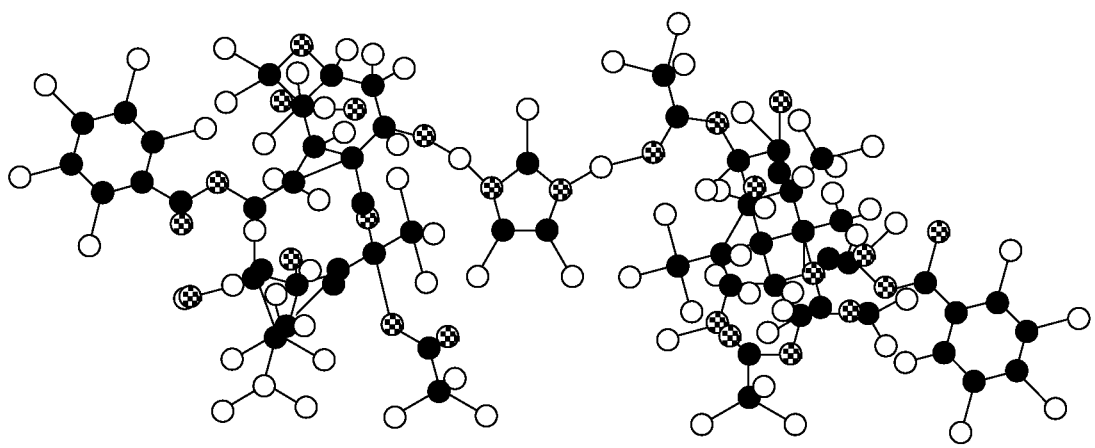

(IA)

In view of the above, it is clear that the objects of the invention are achieved.

As various changes could be made in the above composition and process without departing from the scope of the invention, it is intended that all matter contained in the above description be interpreted as illustrative and not in a limiting sense.

What is claimed:

1. A crystalline complex of baccatin III and imidazole exhibiting essentially the following x-ray diffraction pattern:

| Line | Spacing d (Å) | Relative Intensity |
|---|---|---|
| 1 | 10.52 | 30 |
| 2 | 9.57 | 30 |
| 3 | 8.95 | 100 |
| 4 | 6.95 | 20 |
| 5 | 6.60 | 10 |
| 6 | 6.24 | 20 |
| 7 | 5.61 | 10 |
| 8 | 5.20 | 40 |
| 9 | 4.82 | 40 |
| 10 | 4.13 | 50 |
| 11 | 3.90 | 20 |
| 12 | 3.75 | 10. |

2. A crystalline complex of baccatin III and 2-methylimidazole exhibiting essentially the following x-ray diffraction pattern:

-continued

| Line | Spacing d (Å) | Relative Intensity |
|---|---|---|
| 11 | 3.89 | 10 |
| 12 | 3.75 | 20 |
| 13 | 3.73 | 10. |

3. A crystalline complex of baccatin III and isopropanol exhibiting essentially the following x-ray diffraction pattern:

| Line | Spacing d (Å) | Relative Intensity |
|---|---|---|
| 1 | 10.52 | 30 |
| 2 | 9.24 | 20 |
| 3 | 8.52 | 100 |
| 4 | 7.19 | 20 |
| 5 | 6.60 | 20 |
| 6 | 6.13 | 20 |
| 7 | 5.35 | 10 |
| 8 | 5.03 | 30 |
| 9 | 4.70 | 25 |
| 10 | 4.09 | 50 |
| 11 | 3.78 | 20 |
| 12 | 3.72 | 20 |
| 13 | 3.56 | 20 |
| 14 | 3.24 | 10 |

-continued

| Line | Spacing d (Å) | Relative Intensity |
|------|---------------|--------------------|
| 15   | 3.12          | 10                 |
| 16   | 2.95          | 10                 |
| 17   | 2.83          | 20.                |

4. A process for preparing the complex of claim 1 or 2, which comprises interacting a solution of baccatin II in a organic solvent with imidazole or 2-methylimidazole or a solution of imidazole or 2-methylimidazole in an organic solvent, collecting a formed precipitate of the complex by filtration and then drying the precipitate.

5. The process of claim 4, wherein the organic solvent for baccatin III or the imidazole or 2-methylimidazole is methylene chloride, ethyl acetate, n-butyl acetate or dichloroethane.

6. A process for liberating baccatin III from the complex of claim 1 or 2, comprising the steps of:
   a) mixing the complex with a mixture of organic solvent and water;
   b) separating the organic solvent;
   c) washing the organic solvent with water;
   d) drying the organic solvent; and
   e) finally evaporating the organic solvent to give baccatin III.

7. The process of claim 6, wherein the organic solvent is methylene chloride, dichloroethane, ethyl acetate, or n-butyl acetate.

8. A method of isolating baccatin III from a broth of a plant cell culture containing other taxanes, comprising the steps of:
   a) interacting the broth with an imidazole or 2-methylimidazole or a solution of an imidazole or 2-methylimidazole dissolved in an organic solvent;
   b) collecting a formed precipitate of a complex of baccatin III and imidazole or 2-methylimidazole by filtration;
   c) drying the precipitate of the complex;
   d) breaking the precipitate of the complex with an organic solvent and water;
   e) separating the organic solvent;
   f) washing the organic solvent with water;
   g) drying the organic solvent; and
   h) finally evaporating the organic solvent to give baccatin III.

9. The method of claim 8, wherein the organic solvent of the broth is n-butyl acetate, ethyl acetate, dichloromethane, or dichloroethane.

10. The method of claim 8, wherein the imidazole or 2-methylimidazole is dissolved in methylene chloride, n-butyl acetate, ethyl acetate, or dichloroethane.

11. The method of claim 8, wherein the organic solvent for breaking the precipitate of the complex is methylene chloride, n-butyl acetate, ethyl acetate, or dichloroethane.

12. The method of claim 8, wherein the culture contains baccatin III in admixture with paclitaxel.

13. A method of isolating baccatin III from an organic solvent plant extract of bark or needles of yew trees containing baccatin III in admixture with other taxanes, comprising the steps of:
   a) interacting the organic solvent plant extract with an imidazole or 2-methylimidazole or an imidazole or 2-methylimidazole dissolved in an organic solvent;
   b) collecting a precipitate formed of a complex of baccatin III and imidazole or 2-methylimidazole by filtration;
   c) drying the precipitate of the complex:
   d) breaking the complex with an organic solvent and water;
   e) separating the organic solvent;
   f) washing the organic solvent with water;
   g) drying the organic solvent; and
   h) finally evaporating the organic solvent to give baccatin III.

14. The method of claim 13, wherein the organic solvent of the plant extract is n-butyl acetate, methylene chloride, methanol, dichloroethane, or ethyl acetate.

15. The method of claim 13, wherein the imidazole or 2-methylimidazole is dissolved in methylene chloride, n-butyl acetate, ethyl acetate, or dichloroethane.

16. The method of claim 13, wherein the organic solvent for breaking the complex is methylene chloride, n-butyl acetate, ethyl acetate, or dichloroethane.

17. The method of claim 13, wherein the extract contains baccatin III in admixture with paclitaxel.

18. A method of purifying solid baccatin III by heating said baccatin III in isopropanol until a solution is formed and then cooling the solution to form a solid complex of baccatin III and isopropanol.

19. A method of liberating baccatin III from the isopropanol complex by heating in an organic solvent.

20. The method of claim 19 wherein the organic solvent is acetonitrile.

* * * * *